(12) United States Patent
Patel et al.

(10) Patent No.: US 6,582,447 B1
(45) Date of Patent: Jun. 24, 2003

(54) CONVERTIBLE BLOOD CLOT FILTER

(75) Inventors: Nilesh Patel, Fishers, IN (US); Kenneth P. Moresco, Alexandria, VA (US); William M. Appling, Hartford, NY (US)

(73) Assignee: AngioDynamics, Inc., Queensbury, NY (US)

( * ) Notice: Subject to any disclaimer, the term of this patent is extended or adjusted under 35 U.S.C. 154(b) by 188 days.

(21) Appl. No.: 09/693,412

(22) Filed: Oct. 20, 2000

(51) Int. Cl.[7] ............................................. A61M 29/00
(52) U.S. Cl. ......................................................... 606/200
(58) Field of Search ........................................ 606/200

(56) References Cited

U.S. PATENT DOCUMENTS

| | | | |
|---|---|---|---|
| 4,580,568 A | 4/1986 | Gianturco | |
| 4,688,553 A | 8/1987 | Metals | |
| 4,793,348 A | 12/1988 | Palmaz | |
| 5,035,706 A | 7/1991 | Giantureo et al. | |
| 5,383,887 A | 1/1995 | Nadal | |
| 5,549,626 A | 8/1996 | Miller et al. | |
| 6,241,746 B1 | 6/2001 | Bosma et al. | |
| 6,267,776 B1 * | 7/2001 | OConnell | 606/200 |
| 6,267,777 B1 | 7/2001 | Bosma et al. | |

* cited by examiner

Primary Examiner—John Fox
(74) Attorney, Agent, or Firm—Reed Smith LLP

(57) ABSTRACT

A vena cava blood clot filter is described that is attached to the walls of the vena cava by barbed anchors. In its filtering state, the filter is cone shaped which causes the blood to be filtered. The cone shape is formed by an appropriate restraining mechanism. When it is desired to stop filtering, the restraining mechanism is released and the filter takes a cylindrical shape. The cylindrical shaped filter will then line the vena cava wall and cease filtration of the blood.

21 Claims, 11 Drawing Sheets

CONVERTIBLE BLOOD CLOT FILTER

BACKGROUND

1. Field of the Invention

The following invention relates to a clot filter and more specifically to a convertible vena cava blood clot filter.

2. Description of the Related Art

Vena cava blood clot filters are generally placed in the inferior vena cava, introduced either through the femoral or jugular vein. These filters trap blood clots that have arisen from the peripheral veins and that travel through the vena cava. By trapping the blood clots, the filter prevents the clots from lodging in the pulmonary bed, which can lead to a condition known as pulmonary embolus.

Pulmonary embolus (PE) has long been recognized as a major health care concern. Untreated PE is associated with a high mortality rate, widely held to be approximately 30%, although the exact rate is unknown. Symptomatic PE, however, represents only one manifestation of a more protean disorder, venous thromboembolic disease (VTD), which includes both deep venous thrombosis (DVT) and PE. Understanding of the interrelationship of these disorders has increased in recent years, as has the extent to which VTD contributes to patient mortality.

The current standard of care of VTD is anticoagulation for a minimum period of six months. If patients are properly treated with anticoagulation, the impact of VTD upon patient health is minimized. However, anticoagulant therapy carries the risk of bleeding complications. In patients with VTD or PE that 1) are at high risk of developing a bleeding complication, 2) have a contraindication to anticoagulant therapy, 3) had a failure of response to anticoagulant therapy (i.e. further episodes of PE), or 4) developed a bleeding complication because of anticoagulant therapy, vena cava blood clot filters play an important role in the management of VTD.

Vena cava clot filters can be categorized into two device families: permanently implanted devices and temporary devices. Permanently implanted devices are implanted for patients that require a filter for more than fourteen days. Fourteen days roughly approximates the time before which the points where the filter contact with the caval wall becomes covered by endothelial cells which thicken to eventually attach the filter permanently to the cava wall. If an attempt is made to remove the filter after this time point, severe damage may occur resulting in laceration or rupture of the vena cava, or at the very least, a focal disruption of the endothelial lining which may predispose to caval stenosis, thrombosis (clot formation) or occlusion.

Since the permanent blood clot filters are left in the body for the lifetime of the patient, the patient undergoes several risks that continue throughout the person's lifetime. The reported long-term sequela of some of the permanent devices include thrombotic occlusion of the vena cava, filter migration, filter fragmentation and filter embolization.

These problems can occur because the blood clot filter is directly in the blood stream and continually filtering the blood clots throughout the lifetime of the patient. Thrombotic occlusion and filter embolization can occur when a gradual buildup of blood clots forms in or around the filter due to the continuous filtering. Filter migration and filter fragmentation can occur because of the constant impact between the blood filter and the flowing blood can move the filter or break the structure of the filter.

Temporary blood clot filters do not share those long-term risks because they are removed from the patient's body. However, the situations in which temporary blood clot filters are used are limited. The patient must recover to the point that the risk from PE is reduced to an acceptable level prior to the 14-day limit or to a time point at which the patient may be safely anticoagulated. Otherwise, a permanently implanted blood clot filter must be used to avoid damage to the caval wall that may result if attempt is made in removal after 14-days.

Temporary blood clot filters fall into two categories. One group utilizes a permanently attached tethering catheter for retrieval, whereas the other requires the use of a retrieval device for removal. In addition to the limited amount of time that it can remain in the vena cava, the catheter-based design has the draw back of infectious complications at the entry site. Other temporary designs allow a filter to be placed and later retrieved using a device.

When a patient's need for a blood clot filter is known to be temporary, but longer than the 14-day period, the patient's only recourse is to receive a permanent blood clot filter. An example of a temporary need resulting in placement of a permanent vena cava blood clot filter is a patient who need needs protection from PE in the perioperative period or a woman with DVT during pregnancy. These patients will receive a permanent filter and be unnecessarily subjected to the lifelong risks associated with permanent blood clot filters.

Accordingly, it is the object of the present invention to disclose an implanted device that provides effective caval filtration for any length of time. However, if and when it is determined that the risk from the implanted device disrupting laminar blood flow exceeds the risk of further PE, the filter can be removed from the blood stream to eliminate the associated risks of having a permanent filter within the bloodstream. This can be done at any time without regard to the amount of time that the filter has been implanted and without causing damage to the caval wall. Another object of the present invention is to provide such a filter that allows trapping (capturing) of blood clots of sizes that result in a clinically significant PE that poses an unacceptably high risk of patient morbidity and mortality. The trapped clots in the filter are then dissolved by the bodies own intrinsic fibrinolytic system, without causing pulmonary function compromise. Still a further object of the present invention is to provide such a filter that is relatively simple in design and is relatively inexpensive to manufacture.

SUMMARY OF THE INVENTION

The present invention provides a blood clot filter and a method for its use. The blood clot filter comprises an expandable filter shaped in the form of a cylinder. The filter is composed of high memory wire and the wire is formed into a band of zigzag bends.

In its pre-deployment form, both ends of the filter are collapsed to form a slender wire construct. After deployment, one end of the cylinder is held together by a suitable restraining means such as a Teflon ring with a diameter of approximately 3 mm. The other end of the cylinder is expanded and has a sufficiently large diameter to contact the walls of the inferior vena cava with sufficient force to hold the filter in place against the inferior vena cava. Additional means are used to attach that end of the filter to the walls of the vena cava.

When it is desirable to stop filtering, the Teflon ring holding the narrower end of the filter is broken thereby releasing the end of the filter. Once released, the narrow end of the filter will expand until the entire filter lines the walls of the vena cava. The filter will no longer filter the blood nor will it be directly in the blood stream.

BRIEF DESCRIPTION OF THE DRAWINGS

The accompanying drawings are included to provide an understanding of the invention and constitute a part of the specification.

DESCRIPTION OF THE INVENTION

Figure 1:
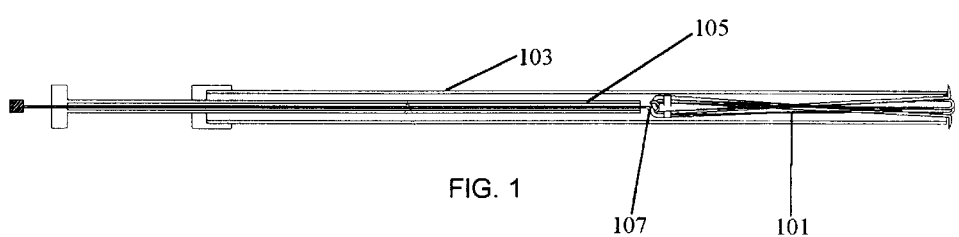
FIG. 1 depicts a side view of a deployment device for the blood clot filter in accordance with the present invention.

Referring now to the detailed drawings, wherein like numerals are used to denote like elements, a description of the embodiments will be discussed. FIG. 1 depicts a filter delivery catheter that can be used in implanting the blood clot filter 101 within the vena cava. The filter 101 is collapsed into a small slender profile container within an outer tube 103. The outer tube 103 of the delivery catheter retains the blood clot filter 101 in this collapsed state and provides a substantial amount of the column strength of the delivery catheter.

An inner tube 105 is used to push the filter 101 out of the outer tube 103. A retention hook wire 107 is attached to the filter 101 and allows the user to pull the filter back into the delivery system if the position, while deploying the filter 101, is not satisfactory. Once the filter 101 is completely out of the outer tube 105, the hook is advanced, turned and retracted. A hub system (not shown) at the proximal end of the delivery catheter will allow the user to easily operate the system.

To implant the filter, the delivery catheter is placed percutaneously into the jugular vein. The delivery catheter is advanced through the Superior Vena Cava, through the right heart, and into the Inferior Vena Cava. The filter 101 can be seen by fluoroscopy. To deploy, the filter will be held in place by maintaining position of the inner tube 103. The outer tube 103 is retracted, thus uncovering the filter and allowing it to open. If the operator does not like the position of the filter 101, the retention wire can be used to pull the filter back into the sheath for repositioning.

Figure 2:
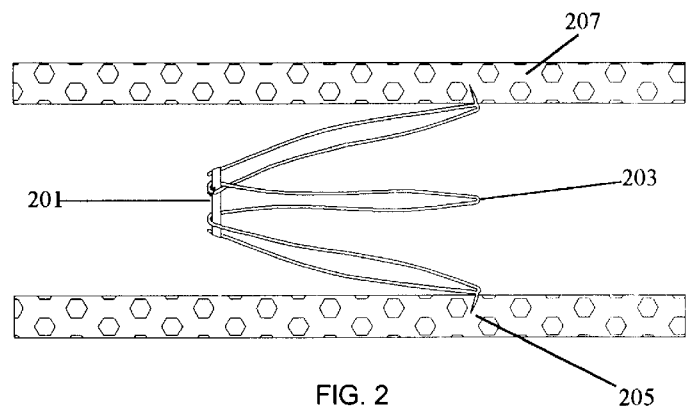
FIG. 2 depicts a side view of the first embodiment of a blood clot filter deployed in accordance with the present invention.

FIG. 2 shows the blood clot filter 101 properly implanted within the vena cava 207. The filter 101 is an expandable structure that is normally in the shape of a cylinder. The body of the filter 101 is composed of a high memory wire predisposed to the fully expanded position. The wire of the filter 101 is formed in a zigzag pattern. FIG. 2 depicts the filter 101 in its deployment phase in which it is held to the shape of a cone.

A ring 201 holds one end of the filter together. The ring 201 can be composed of Teflon or other suitable material such as polytetrafluoroethylene that is resilient enough to withstand constant abrasion from the blood flow, but still capable of being broken with minimal force when desired. The ring 201 restricts the end of the filter 101 to a 3 mm diameter. In this position, the filter will be able to capture blood clots greater than 3 mm. The diameter of the ring 201 can be any diameter to adjust the size of the blood clots captured. The expandable nature of the filter 101 will accommodate different diameters established by the ring 201.

The other end of the filter 101 is fully expanded to the diameter of the vena cava 207. Shaped as such, the wire forms a plurality of legs 203 that contact the vena cava wall at the apices of the legs. Barbed anchors 205 are placed at each apex of each leg 203 to keep the filter in the intended location. The filter 101 is placed so that the conical end of the filter 101 is just below the renal veins. The barbed anchors 205 are angled so that the blood flow will impact the filter 101 and push the barbed anchors into the caval wall.

Using a conical shape allows for the efficient filtering of the blood. The highest velocity of flow is in the center of the blood stream and most blood clots will flow through the center to be caught by the ring. The legs 203 can be adjusted to vary the spacing between and leg to facilitate filtering. In addition, the legs 203 of the filter in this position will streamline the blood clots into the center of the filter 101.

Figure 3:
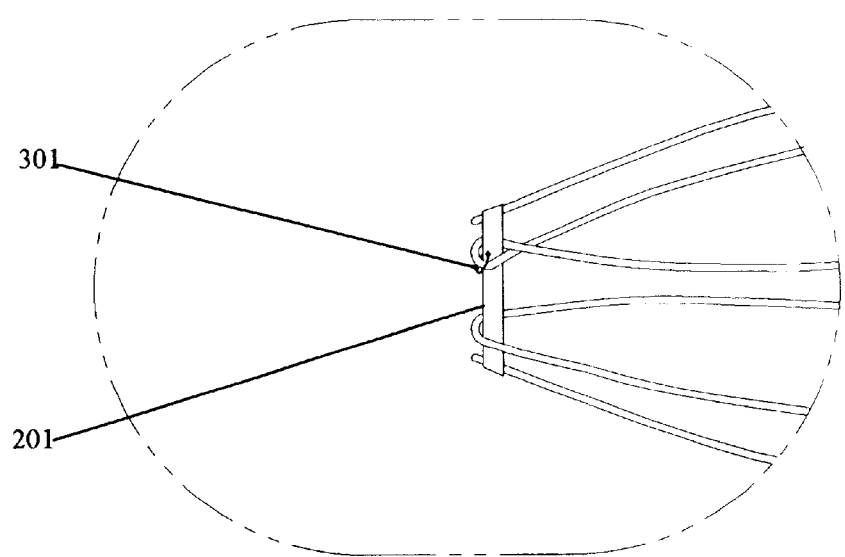
FIG. 3 depicts a magnified side view of the narrow end of a blood clot filter of the first embodiment.
Figure 4:
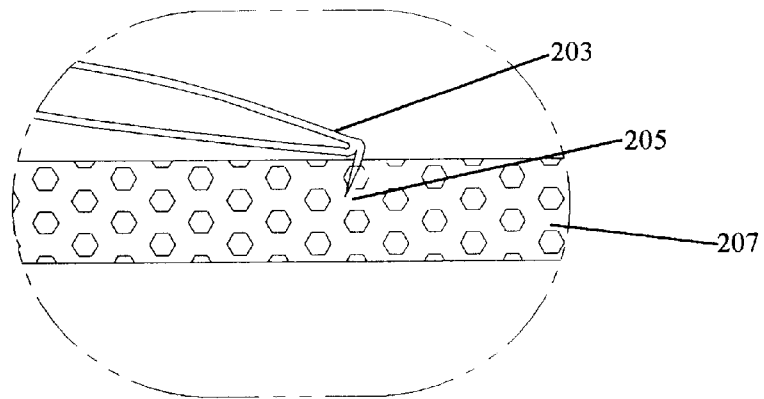
FIG. 4 depicts a magnified view of a portion of the blood clot filter showing the barbed anchor in accordance with the present invention.

FIG. 3 depicts a magnified view of the narrower end of the filter 101. A tie 301 attaches the ring 201 to the filter 101. The tie 301 will hold on to the ring 201 when the ring is broken and the filter 101 expands to its cylindrical form. Consequently, the tie 301 is wrapped around the filter wire such that the tie 301 cannot be dislodged from the filter without breaking the tie 301. The tie 301 is also securely connected to the ring by creating a hole in the middle of the ring band and looping the tie 301 through that hole. Tie 301 can be composed of Teflon or any other material that can withstand the abrasion of the blood flow and not break from it. FIG. 4 depicts the barbed anchor that is used to attach the filter 101 to the vena cava wall.

Figure 5:
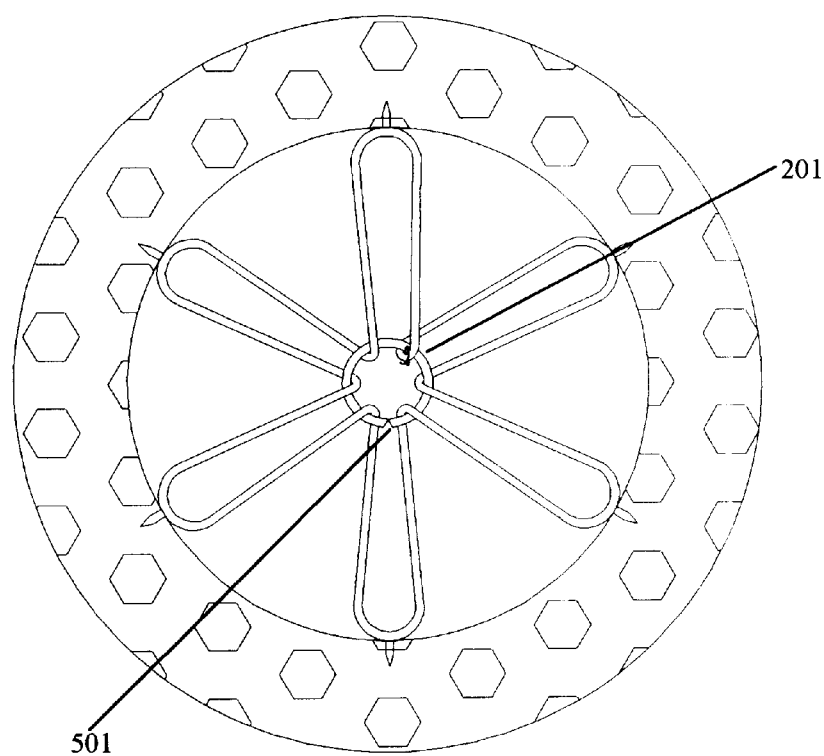
FIG. 5 depicts a front view of the first embodiment of the blood clot filter deployed in accordance with the present.

FIG. 5 shows the filter 101 from the front view. Ring 201 has a notch 501 that weakens the ring such that the ring 201 will break at the point of notch 501 when stretched beyond its limits. The location of the notch 501 can be anywhere on the ring 201. It can be diametrically opposed to the tie 301 to ensure that the ring 201, when broken, will have equal portions to either side of the tie 301. The broken ring will then be less obtrusive to the blood flow in the vena cava. The notch 501 should be large enough to ensure that the break will occur at the notch and not at the point at which the tie 301 is connected to the ring 201.

Figure 6:
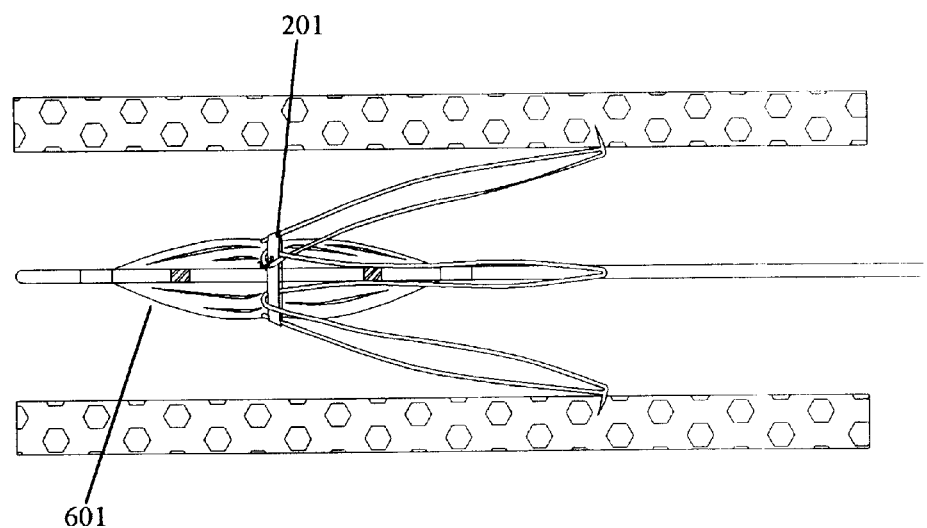
FIG. 6 depicts a side view of the engagement of a balloon angioplasty catheter with the first embodiment of the blood clot filter.

When it is determined that the disadvantages of filtering blood clots outweighs the benefits, then the ring 201 will be broken to release the filter from its conical shape to its cylindrical shape. FIG. 6 depicts one process by which the filter 101 is released from the ring 201. A balloon angioplasty catheter 601 that has a large enough diameter is placed into the vena cava and inserted into the ring 201. The balloon catheter 601 is then inflated until the ring 201 breaks at the position of notch 501. The balloon catheter will then be extracted from the patient's body.

Figure 7:
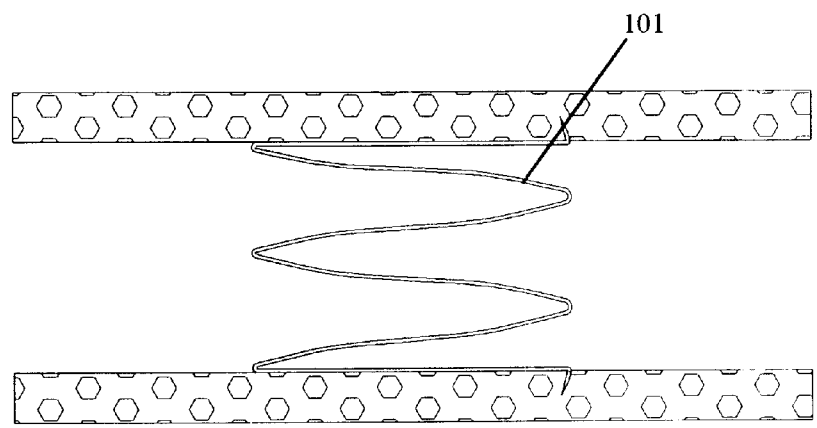
FIG. 7 depicts a side view of the blood clot filter after the filter has been changed to its non-filtering state in accordance with the present invention.
Figure 8:
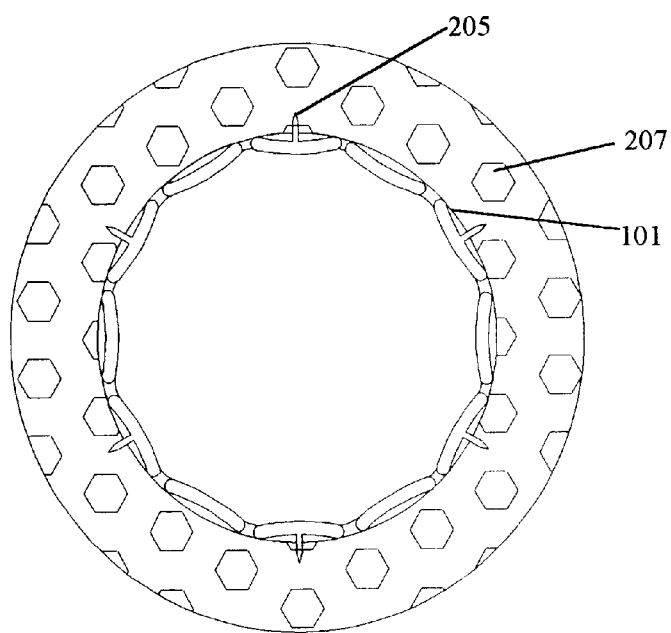
FIG. 8 depicts a front view of the blood clot filter after the filter has been changed to its non-filtering state in accordance with the present invention.

Upon breaking the ring, the filter 101 expands into its normal cylindrical shape. The expanded filter is shown in FIGS. 7–8. In this position, the filter will hug the walls of the vena cava and not be directly in the blood stream to filter the blood for blood clots. The filter is essentially converted into a stent device. The thickened endothelial cells around the apices of the legs of the filter will remain around the apices since the device will not be removed.

In keeping the filter within the patient and causing it to line up against the vena cava wall, endothelial cells will also develop around the entire filter and the filter will eventually grow into the caval wall. This will eliminate the risks that are usually present when keeping the filter directly in the blood stream and constantly filtering for blood clots. Any potential risk from potential thrombus formation due to laminar blood flow disruption and risk from device fracture or fragment embolization during the patients' life will not be present.

Figure 9A:
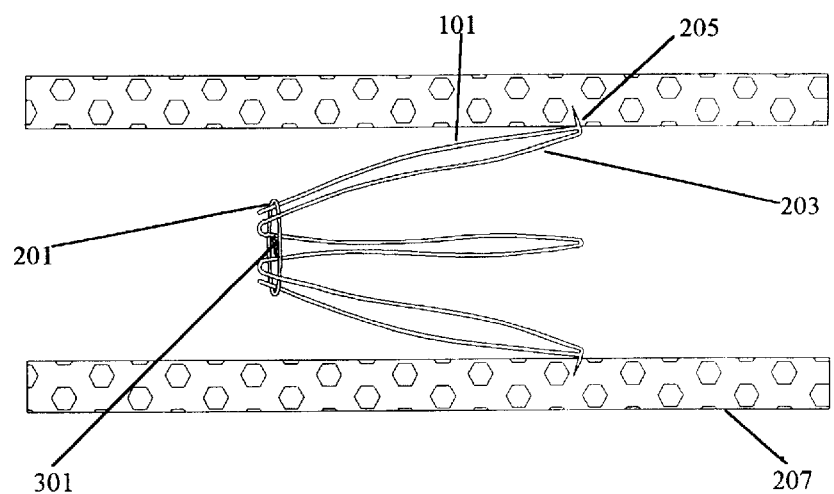
FIG. 9A depicts a side view of a second embodiment of a blood clot filter using a tied suture in accordance with the present invention.
Figure 9B:
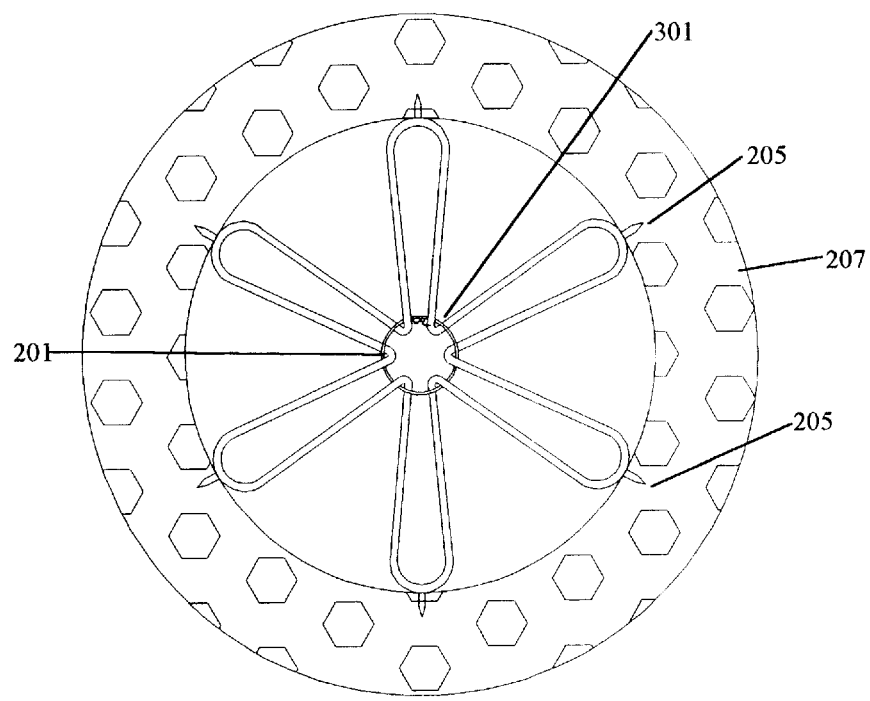
FIG. 9B depicts a front view of the second embodiment of a blood clot filter using a tied suture in accordance with the present invention.

FIGS. 9A–9B depict a second embodiment of the present invention. Filter 101 is presented in its deployed form. Ring 201 retains the narrow end of the filter 101 in its conical shape and is intertwined with the wire of the filter such that the ring will not be dislodged from the filter body. Ring 201 is shown as a tied suture. Tie 301, however, is not connected to the filter 101. Not connecting the ring 201 to the filter 101 via tie 301 allows the ring 201 to be completely removed after the ring 201 has been broken.

Figure 10A:
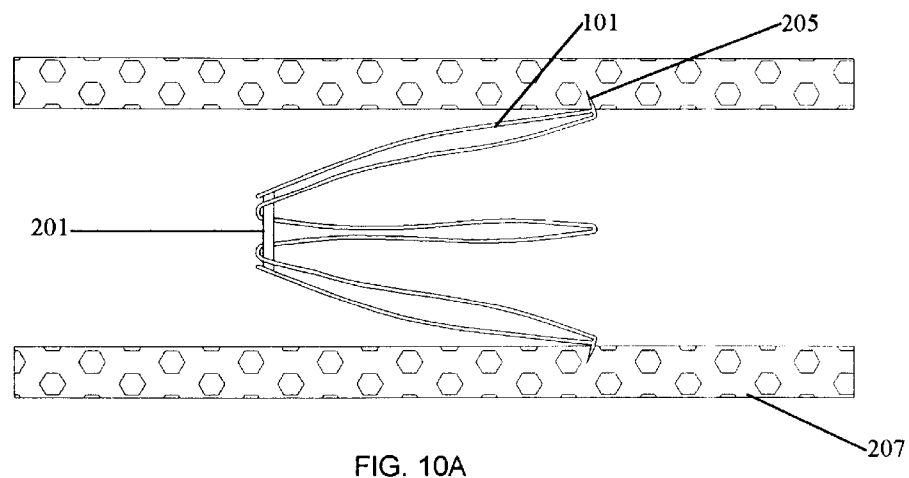
FIG. 10A depicts a side view of the second embodiment of a blood clot filter using a unitary ring in accordance with the present invention.
Figure 10B:
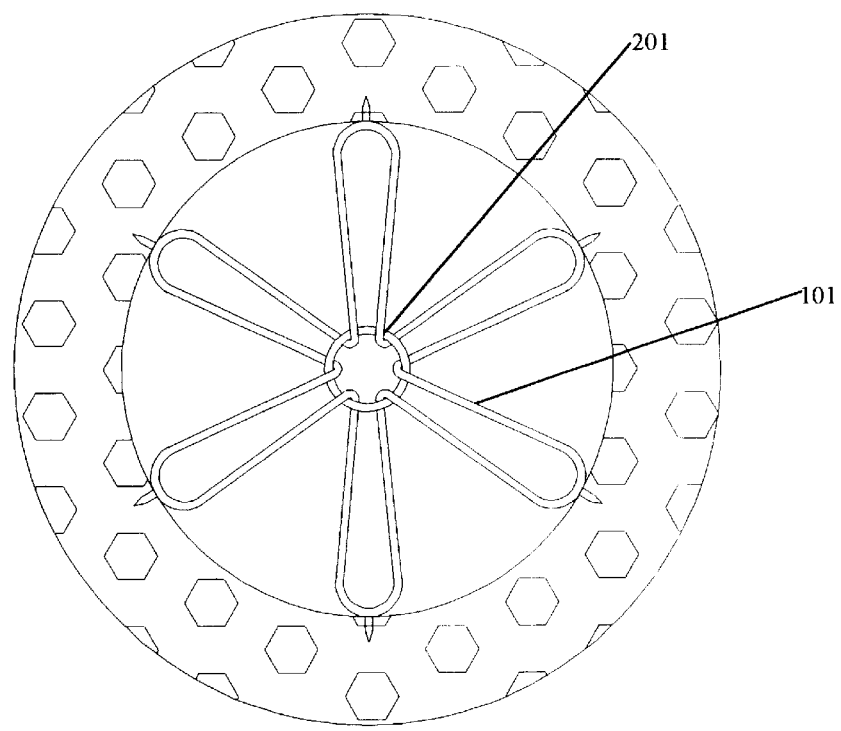
FIG. 10B depicts a front view of the second embodiment of a blood clot filter using a unitary ring in accordance with the present invention.
Figure 11A:
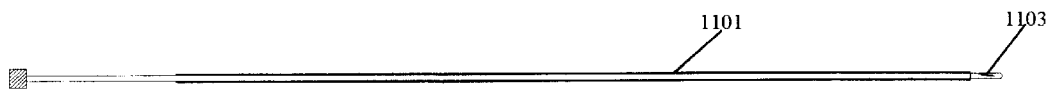
FIG. 11A depicts a side view an endovascular device used to change the filter to its non-filtering state in accordance with the present invention.
Figure 11B:
FIG. 11B depicts a top view of an endovascular device used to change the filter to its non-filtering state in accordance with the present invention.
Figure 11C:
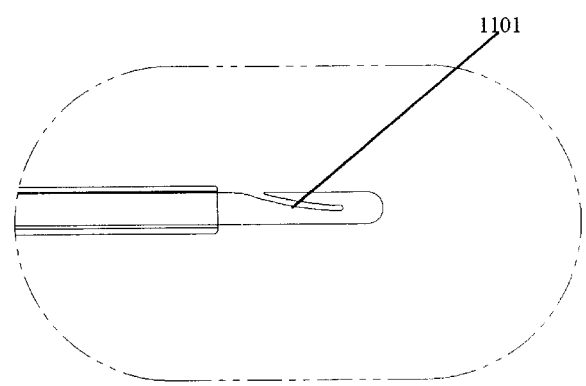
FIG. 11C depicts a magnified side view an endovascular device used to change the filter to its non-filtering state in accordance with the present invention.
Figure 11D:
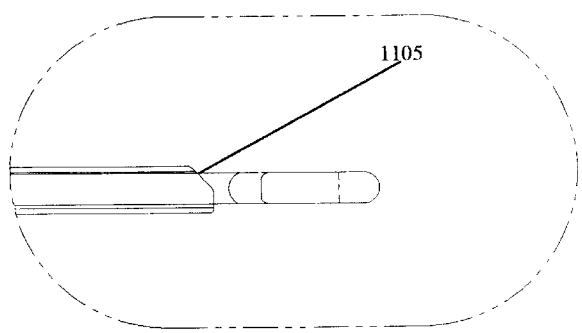
FIG. 11D depicts a magnified top view of an endovascular device used to change the filter to its non-filtering state in accordance with the present invention.

FIGS. 10A and 10B depict a modification of the second embodiment that uses a unitary ring 201, rather than a tied suture, to contain the conical end of the filter 101. The unitary ring 201 is slid over the barbed end by weaving it over and under alternating leg sets. The ring is slid fully to the opposite end where it remains in position holding the conical end of the filter in the constrained position. The advantage of this simple unitary ring is there is no knot that can be prone to premature failure. The ring is also the lowest profile design providing minimal turbulent formation in the blood stream. The ring in this design also does not have a predetermined break zone that may be prone to premature failure.

The ring removal device depicted in FIGS. 11A–11D will cut the ring 201 to release the filter 101 and remove it from the patient. Ring removal device has a hook 1103 that will act to grab the ring 201. The size of the opening to the hook 1103 is smaller than the diameter of the wire, but is larger than the ring material. After grabbing the ring 201, hook 1103 will be retracted into the outer tube of the device. The outer tube has a sharp portion 1105 that will cut the ring 201 when the hook is being retracted. Upon cutting the ring 201, ring removal device 1101 will extract the ring 201 from the filter to be removed from the patient. In removing the ring 201, it minimizes the amount of foreign material present within the body to be absorbed and eliminates any potential obstruction of the blood flow.

Figure 12:
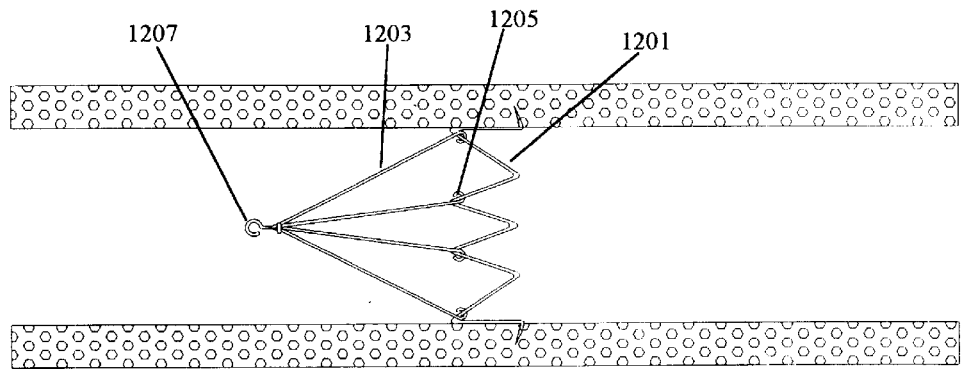
FIG. 12 depicts a side view of a third embodiment of a blood clot filter deployed in accordance with the present invention.
Figure 13:
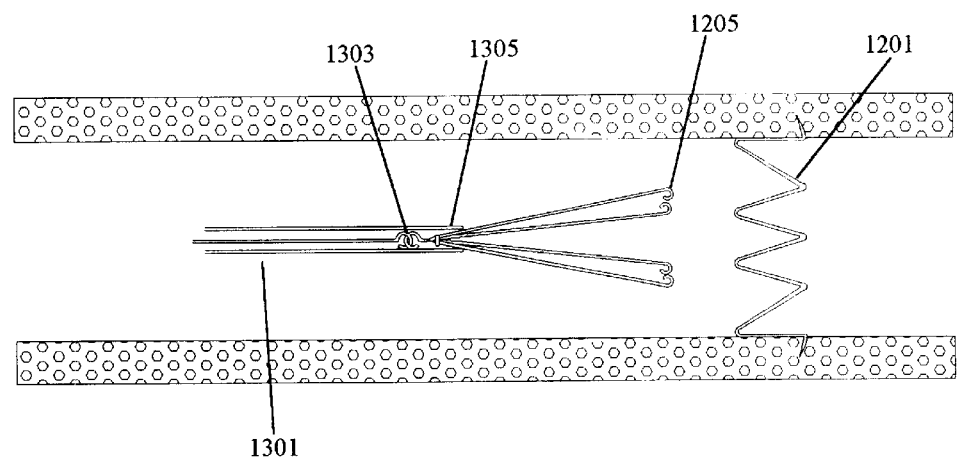
FIG. 13 depicts the disengagement of a portion of the blood clot filter in accordance with the present invention.

FIGS. 12 and 13 depict a third embodiment of the present invention. Filter 101 is composed of two pieces, the base section 1201 and the filter section 1203. The base section 1201 is cylindrical in shape and completely lines the walls of the cava vena. Barbed anchors hold the base section in place against the caval wall.

The filter section 1203 is shaped into a cone and has a hooked portion 1205 at the end of each leg 1203. This hooked portion 1205 will engage with corresponding bends in the wire of the base section 1201. The blood flow will push the hooked portions 1205 against the bent wire to hold the filter section 1203 connected to the base section 1201. At the apex of the cone, a disengaging hook 1207 is placed.

To disengage the filter section 1203 from the base section 1201, a removal device 1301 is inserted. The removal device 1301 can have a hook 1303 contained within an outer tube 1305. The removal device is maneuvered over the disengaging hook 1207 of the conical filter section 1203. When inserted into the removal device, the disengaging hook 1207 will engage with the hook 1303. Outer tube 1305 will contact the legs of the filter portion and exert an inwardly radial force on the legs 1203 thereby forcing the hooked portions 1205 of the legs 1203 to disengage from the base section 1201. Once disengaged from the base section, the filter section can be completely drawn into the removal device 1301 and safely removed from the patient's body. The base section 1201 will remain within the patient's body and be incorporated into the vena cava.

Figure 14:
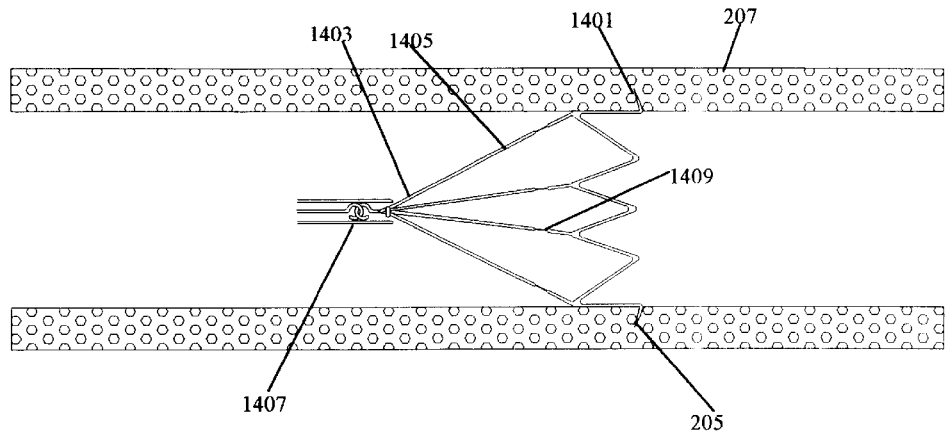
FIG. 14 depicts a side view of a fourth embodiment of a blood clot filter deployed in accordance with the present invention.
Figure 15:
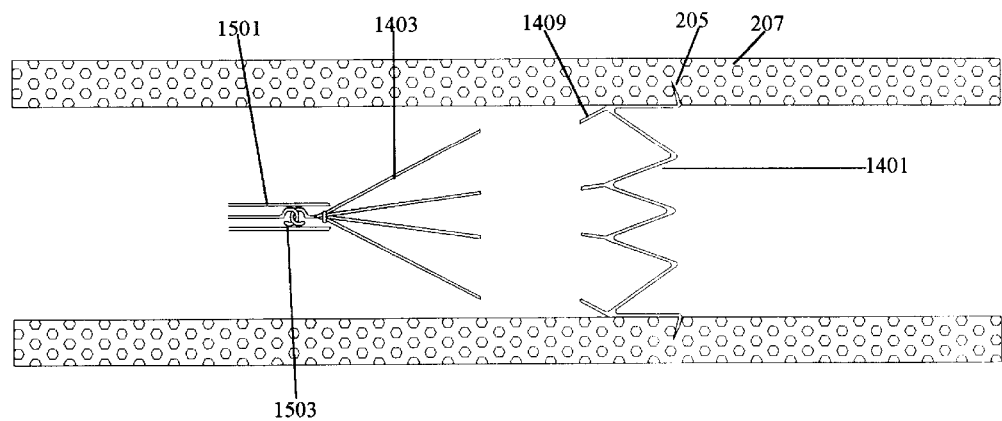
FIG. 15 depicts the disengagement of a portion of the blood clot filter in accordance with the present invention.

FIGS. 14 and 15 depict a fourth embodiment of the present invention. Similar to the third embodiment, the filter 101 is composed of two pieces, the base section 1401 and the filter section 1403. Legs 1405, however, contain weakened sections that are predisposed to be broken when desired. The weakened sections can be designed to be broken by the application of a low voltage electrical current or be a physically weaker substance. FIG. 15 depicts the removal device to be used for the fourth embodiment in which hook 1503 engages disengaging hook 1407 and filter section 1403 breaks off at predetermined weakened sections 1409. Once completely broken off, the filter section 1403 can be retracted into the removal device and extracted from the patient.

Figure 16:
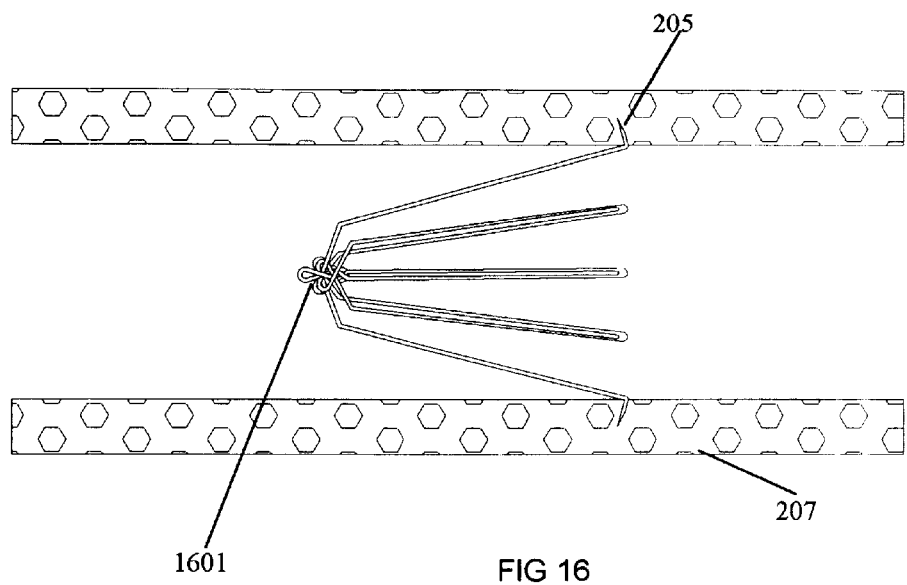
FIG. 16 depicts a side view of a fifth embodiment of a blood clot filter in accordance with the present invention.
Figure 17:
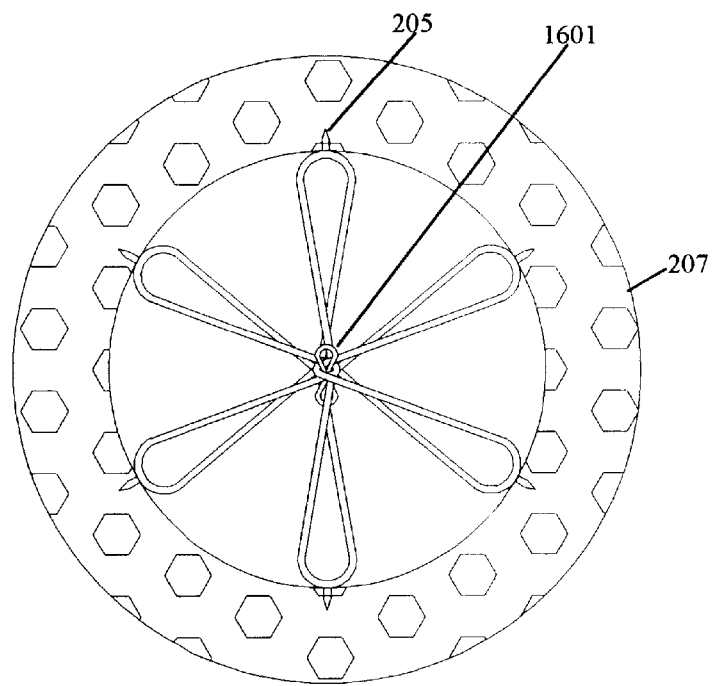
FIG. 17 depicts a front view of a fifth embodiment of a blood clot filter in accordance with the present invention.

FIGS. 16 and 17 depict yet another embodiment of the present invention. Filter 101 is composed of a single wire structure and shaped in the form of a cone to filter the blood stream. At the narrow end of the filter, the apex of each return bend is shaped in a loop of approximately 1 mm inside diameter. Stacking all of the loops on top of each other forms the conical end. A hitch pin 1601 is inserted through all the loops and holds the loops and the filter legs in the filtering conical shape. The hitch pin 1601 is retains its position in the loops by an interference fit. The hitch pin 1601 is also designed so that the pin can be grasped or hooked by a tool, pulled from its position, and removed from the body when the physician determines that clot filtering is not needed any longer.

Once the hitch pin 1601 is pulled form the loops, the filter springs open to its cylindrical non-filtering position. The hitch pin 1601 is formed of a high memory wire in an "infinity symbol" shape with the dimension across the shape of 1.1 mm, or greater than the 1 mm inside dimension of the loops at the filter strut apexes. The hitch pin 1601 also incorporates a densely radiopaque marker to aid the physician while attempting to grasp the pin under fluoroscopic guidance. This "infinity" design allows the hitch pin 1601 to be pulled from either direction. The physician can choose the best direction at the time of conversion based on patient factors.

Other pin designs can be produced essentially performing the same function. A modification of this design is the use of biodegradable materials to form the pin. The hitch pin 1601 can be formed from a material that will give a known service life and will open automatically. The hitch pin 1601 can also be formed from a biodegradable material, which requires activation. The hitch pin 1601 can be removed by infusion of an enzyme to dissolve the pin material and open the filter.

Figure 18:
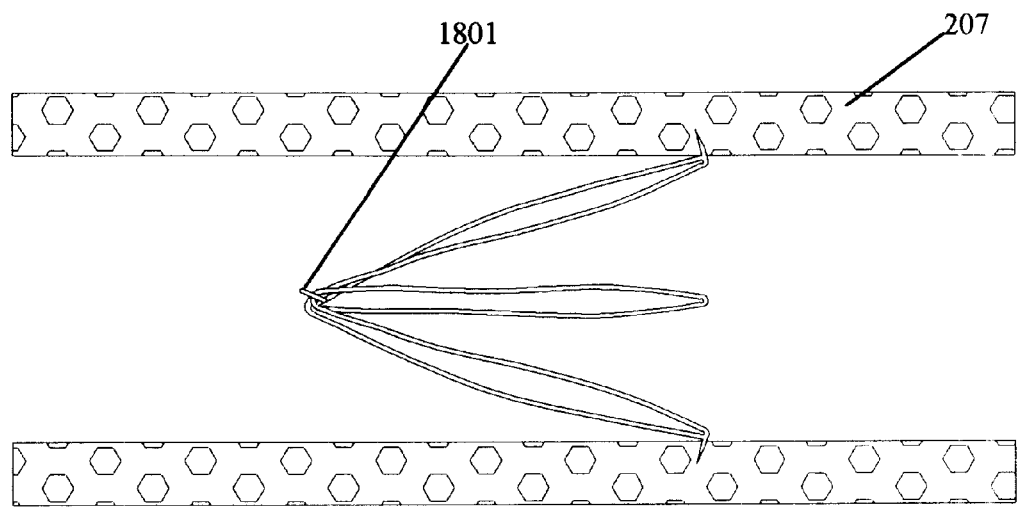
FIG. 18 depicts a side view of a sixth embodiment of a blood clot filter in accordance with the present invention.
Figure 19:
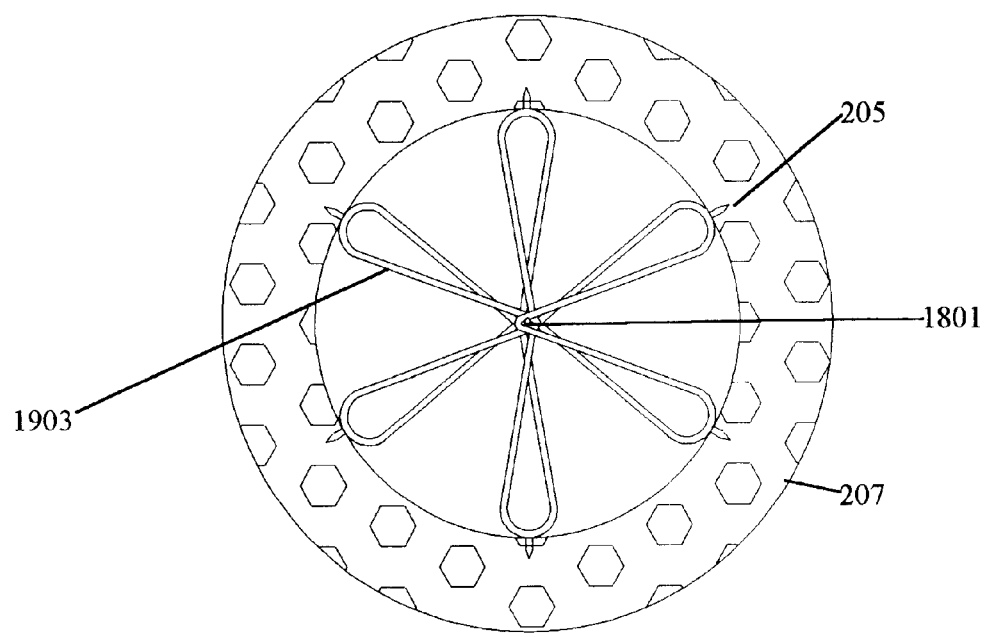
FIG. 19 depicts a front view of a sixth embodiment of a blood clot filter in accordance with the present invention.

FIGS. 18 and 19 depict another embodiment of the present invention. This design does not depend on a second component such as a Teflon ring or removable pin to retain it in its conical deployed position. In this filter design, the apices at the conical end of the filter form an integral latch. At the conical end of the filter, the apexes of five of the six return bends are shaped in loops of approximately 1 mm inside diameter. The sixth apex forms a pin 1801. The conical shape is formed by stacking the five loops on top of each, with the sixth apex inserted through the five loops. The filter is opened to its non-filtering state by grasping the legs of the sixth apex and pulling the pin back and away from the loops. The loops will slide off of the pin 1801 and the filter will open.

The sixth apex has an added densely radiopaque element that can be easily seen by fluoroscopy and can be grasped by biopsy forceps, or other catheter based means. This design has the advantage of having no polymer components that may weaken prematurely, and no components that need to be removed from the body. A latch may be formed by many other configurations of the wire filter body.

The present invention is not to be considered limited in scope by the preferred embodiments described in the specification. Additional advantages and modifications, which readily occur to those skilled in the art from consideration and specification and practice of this invention are intended to be within the scope and spirit of the following claims.

We claim:

1. A blood filter mechanism for use in a vascular lumen comprising:

an implantable filter having an active state and an inactive state;

said filter, when in said active state, being positioned to catch blood clots while said filter is implanted in the vascular lumen; and said filter, when in said inactive state, being positioned to pass blood clots while said filter is implanted in the vascular lumen;

a switching mechanism to switch said filter from said active state to said inactive state comprising a breakable element holding said filter in a position to intercept particles in blood flowing in the vascular lumen to establish said active state;

said filter switched from said active state to said inactive status by breaking said breakable element;

wherein said breakable element remains attached to said filter after said breakable clement is broken.

2. The blood filter mechanism as claimed in claim 1, wherein said filter is biased toward said inactive state.

3. The blood filter mechanism as claimed in claim 1, wherein said breakable element is composed of polytetrafluoroethylene.

4. The blood filter mechanism as claimed in claim 1, wherein said filter is attached to the vascular lumen by a barbed anchor.

5. The blood filter mechanism as claimed in claim 1, wherein said filter forms a conical shape in said active state.

6. The blood filter mechanism as claimed in claim 1, wherein said filter forms a cylindrical shape in said inactive state.

7. The blood filter mechanism as claimed in claim 1, wherein said filter in said active state is sized to pass blood clots less than a predetermined size.

8. The blood filter mechanism as claimed in claim 7, wherein said predetermined size is three millimeters.

9. The blood filter mechanism as claimed in claim 1 wherein said switching mechanism further comprises a balloon angioplasty catheter.

10. The blood filter mechanism as claimed in claim 1 wherein said filter in said inactive state is aligned against the walls of the vascular lumen.

11. A blood filtering method for use in a vascular lumen comprising:

implanting an implantable filter having an active state and an inactive state;

positioning said filter, when in said active state, to catch blood clots while said filter is implanted in the vascular lumen; and positioning said filter, when in said inactive state, to pass blood clots while said filter is implanted in the vascular lumen;

holding said filter in a position with a breakable element to intercept particles in blood flowing in the vascular lumen to establish said active state; and watching said filter from said active state to said inactive status by breaking said breakable element;

wherein said breakable element remains attached to said filter after said breakable element is broken.

12. The blood filtering method as claimed in claim 11, wherein said filter is pre-biased toward said inactive state.

13. The blood filtering method as claimed in claim 11, wherein said breakable element is composed of polytetrafluoroethylene.

14. The blood filtering method as claimed in claim 11, wherein said filter is attached to the vascular lumen by a barbed anchor.

15. The blood filtering method as claimed in claim 11, wherein said filter forms a conical shape in said active state.

16. The blood filtering method as claimed in claim 11, wherein said filter forms a cylindrical shape in said inactive state.

17. The blood filtering method as claimed in claim 11, wherein said filter in said active state is sized to pass blood clots less than a predetermined size.

18. The blood filtering method as claimed in claim 17, wherein said predetermined size is three millimeters.

19. The blood filtering method as claimed in claim 11 wherein said switching method further comprises a balloon angioplasty catheter.

20. The blood filtering method as claimed in claim 11 wherein said switching step further comprises using an endovascular device having a sharp portion capable of cutting said breakable element and a hook portion capable of grabbing said breakable element.

21. The blood filtering method as claimed in claim 11 wherein said filter in said inactive static is aligned against the walls of the vascular lumen.

* * * * *